US011237632B2

(12) United States Patent
Erivantcev et al.

(10) Patent No.: US 11,237,632 B2
(45) Date of Patent: Feb. 1, 2022

(54) RING DEVICE HAVING AN ANTENNA, A TOUCH PAD, AND/OR A CHARGING PAD TO CONTROL A COMPUTING DEVICE BASED ON USER MOTIONS

(71) Applicant: Finch Technologies Ltd., Tortola (VG)

(72) Inventors: Viktor Vladimirovich Erivantcev, Ufa (RU); Alexey Ivanovich Kartashov, Moscow (RU); Iakov Evgenevich Sergeev, Ufa (RU); Gary Stuart Yamamoto, Sacramento, CA (US); Guzel Kausarevna Khurmatullina, Ufa (RU)

(73) Assignee: Finch Technologies Ltd., Tortola (VG)

( * ) Notice: Subject to any disclaimer, the term of this patent is extended or adjusted under 35 U.S.C. 154(b) by 0 days.

(21) Appl. No.: 16/807,444

(22) Filed: Mar. 3, 2020

(65) Prior Publication Data

US 2021/0278898 A1 Sep. 9, 2021

(51) Int. Cl.
*G06F 3/01* (2006.01)
*G06F 1/16* (2006.01)
(Continued)

(52) U.S. Cl.
CPC .............. *G06F 3/014* (2013.01); *A44C 9/02* (2013.01); *A61B 5/0533* (2013.01); *A61B 5/30* (2021.01);
(Continued)

(58) Field of Classification Search
CPC .............. G06F 2203/0331; A44C 9/02; A44C 17/0216; A44C 9/00; A44C 9/0046;
(Continued)

(56) References Cited

U.S. PATENT DOCUMENTS

D455,098 S   4/2002 Stefanelli
6,607,134 B1 * 8/2003 Bard ................. G04B 47/00
                                              235/462.44
(Continued)

FOREIGN PATENT DOCUMENTS

WO    2015102175    7/2015

OTHER PUBLICATIONS

International Search Report and Written Opinion, PCT/US2021/018455, dated Jun. 10, 2021.

(Continued)

*Primary Examiner* — Sanjiv D. Patel
(74) *Attorney, Agent, or Firm* — Greenberg Traurig

(57) ABSTRACT

An apparatus having a ring-shaped housing configured to be wrapped round a finger of a user, the ring-shaped housing having an opening or a joint at a first point round the finger and a first contiguous section that is at a location opposite to the first point across a central axis of the ring-shaped housing; an antenna configured in the ring-shaped housing in the contiguous section; an inertial measurement unit configured to measure motions of the finger; a light-emitting diode (LED) indicator configured on an outer portion of the ring-shaped housing; a charging pad configured to charge a battery configured in the ring-shaped housing; and/or a touch pad configured to receive touch input from a finger of the user.

20 Claims, 5 Drawing Sheets

(51) Int. Cl.
  *H01Q 1/27* (2006.01)
  *G09G 3/32* (2016.01)
  *A61B 5/00* (2006.01)
  *A61B 5/0533* (2021.01)
  *H04B 5/00* (2006.01)
  *H04W 4/80* (2018.01)
  *A61B 5/30* (2021.01)
  *A44C 9/02* (2006.01)

(52) U.S. Cl.
  CPC ............ *A61B 5/6826* (2013.01); *G06F 1/163* (2013.01); *G09G 3/32* (2013.01); *H01Q 1/273* (2013.01); *H04B 5/0012* (2013.01); *H04B 5/0037* (2013.01); *H04W 4/80* (2018.02); *G06F 2203/0331* (2013.01)

(58) Field of Classification Search
  CPC ...... E05B 3/065; E05B 59/00; E05B 63/0056; E05B 63/04
  See application file for complete search history.

(56) References Cited

U.S. PATENT DOCUMENTS

| | | | |
|---|---|---|---|
| 8,605,036 | B1 | 12/2013 | Kelly |
| 9,711,060 | B1* | 7/2017 | Lusted .................. G09B 23/28 |
| 11,042,233 | B2 | 6/2021 | Wang et al. |
| 2003/0142065 | A1 | 7/2003 | Pahlavan |
| 2010/0081900 | A1 | 4/2010 | Price |
| 2010/0188326 | A1* | 7/2010 | Dines ..................... G06F 3/014 |
| | | | 345/156 |
| 2011/0199305 | A1 | 8/2011 | Suh |
| 2012/0218184 | A1* | 8/2012 | Wissmar ............... G06F 3/0346 |
| | | | 345/158 |
| 2013/0135223 | A1 | 5/2013 | Shai |
| 2013/0311798 | A1 | 11/2013 | Sultenfuss et al. |
| 2015/0062086 | A1* | 3/2015 | Nattukallingal ........ G06F 3/016 |
| | | | 345/175 |
| 2015/0133193 | A1 | 5/2015 | Stotler |
| 2015/0220109 | A1 | 8/2015 | Von Badinski et al. |
| 2015/0220145 | A1* | 8/2015 | Elangovan ............ G06F 3/0346 |
| | | | 345/156 |
| 2015/0338916 | A1* | 11/2015 | Priyantha ................ G06F 1/163 |
| | | | 345/173 |
| 2016/0034742 | A1 | 2/2016 | Kim et al. |
| 2016/0066827 | A1 | 3/2016 | Workman et al. |
| 2016/0111037 | A1 | 4/2016 | Kim |
| 2016/0287165 | A1 | 10/2016 | Abreu |
| 2017/0242496 | A1* | 8/2017 | Park ................... G06K 9/00087 |
| 2017/0308165 | A1* | 10/2017 | Erivantcev ............ G06F 3/0346 |
| 2017/0351345 | A1 | 12/2017 | Nirjon et al. |
| 2018/0120892 | A1 | 5/2018 | Von Badinski et al. |
| 2018/0139518 | A1 | 5/2018 | Touma et al. |
| 2018/0225489 | A1 | 8/2018 | Liou et al. |
| 2019/0155385 | A1* | 5/2019 | Lim ..................... H04L 63/0861 |
| 2020/0026352 | A1 | 1/2020 | Wang et al. |
| 2020/0128929 | A1* | 4/2020 | Yep .......................... A44C 9/02 |
| 2020/0266529 | A1* | 8/2020 | Moussakhani ........... H01Q 1/38 |

OTHER PUBLICATIONS

International Search Report & Written Opinion, PCT/US2021/025618, dated Jul. 15, 2021.

* cited by examiner

RING DEVICE HAVING AN ANTENNA, A TOUCH PAD, AND/OR A CHARGING PAD TO CONTROL A COMPUTING DEVICE BASED ON USER MOTIONS

RELATED APPLICATIONS

The present application relates to U.S. patent application Ser. No. 16/576,661, filed Sep. 19, 2019 and entitled "Calibration of Inertial Measurement Units in Alignment with a Skeleton Model to Control a Computer System based on Determination of Orientation of an Inertial Measurement Unit from an Image of a Portion of a User," U.S. patent application Ser. No. 16/044,984, filed Jul. 25, 2018 and entitled "Calibration of Measurement Units in Alignment with a Skeleton Model to Control a Computer System," U.S. patent application Ser. No. 15/973,137, filed May 7, 2018 and entitled "Tracking User Movements to Control a Skeleton Model in a Computer System," U.S. patent application Ser. No. 15/868,745, filed Jan. 11, 2018 and entitled "Correction of Accumulated Errors in Inertial Measurement Units Attached to a User," U.S. patent application Ser. No. 15/864,860, filed Jan. 8, 2018 and entitled "Tracking Torso Leaning to Generate Inputs for Computer Systems," U.S. patent application Ser. No. 15/847,669, filed Dec. 19, 2017 and entitled "Calibration of Inertial Measurement Units Attached to Arms of a User and to a Head Mounted Device," U.S. patent application Ser. No. 15/817,646, filed Nov. 20, 2017 and entitled "Calibration of Inertial Measurement Units Attached to Arms of a User to Generate Inputs for Computer Systems," U.S. patent application Ser. No. 15/813,813, filed Nov. 15, 2017 and entitled "Tracking Torso Orientation to Generate Inputs for Computer Systems," U.S. patent application Ser. No. 15/792,255, filed Oct. 24, 2017 and entitled "Tracking Finger Movements to Generate Inputs for Computer Systems," U.S. patent application Ser. No. 15/787,555, filed Oct. 18, 2017 and entitled "Tracking Arm Movements to Generate Inputs for Computer Systems," and U.S. patent application Ser. No. 15/492,915, filed Apr. 20, 2017 and entitled "Devices for Controlling Computers based on Motions and Positions of Hands," the entire disclosures of which applications are hereby incorporated herein by reference.

FIELD OF THE TECHNOLOGY

At least a portion of the present disclosure relates to computer input devices in general and more particularly but not limited to input devices for virtual reality and/or augmented/mixed reality applications implemented using computing devices, such as mobile phones, smart watches, similar mobile devices, and/or other devices.

BACKGROUND

U.S. Pat. App. Pub. No. 2014/0028547 discloses a user control device having a combined inertial sensor to detect the movements of the device for pointing and selecting within a real or virtual three-dimensional space.

U.S. Pat. App. Pub. No. 2015/0277559 discloses a finger-ring-mounted touchscreen having a wireless transceiver that wirelessly transmits commands generated from events on the touchscreen.

U.S. Pat. App. Pub. No. 2015/0358543 discloses a motion capture device that has a plurality of inertial measurement units to measure the motion parameters of fingers and a palm of a user.

U.S. Pat. App. Pub. No. 2007/0050597 discloses a game controller having an acceleration sensor and a gyro sensor. U.S. Pat. No. D772,986 discloses the ornamental design for a wireless game controller.

Chinese Pat. App. Pub. No. 103226398 discloses data gloves that use micro-inertial sensor network technologies, where each micro-inertial sensor is an attitude and heading reference system, having a tri-axial micro-electromechanical system (MEMS) micro-gyroscope, a tri-axial micro-acceleration sensor and a tri-axial geomagnetic sensor which are packaged in a circuit board. U.S. Pat. App. Pub. No. 2014/0313022 and U.S. Pat. App. Pub. No. 2012/0025945 disclose other data gloves.

U.S. Pat. App. Pub. No. 2016/0085310 discloses techniques to track hand or body pose from image data in which a best candidate pose from a pool of candidate poses is selected as the current tracked pose.

U.S. Pat. App. Pub. No. 2017/0344829 discloses an action detection scheme using a recurrent neural network (RNN) where joint locations are applied to the recurrent neural network (RNN) to determine an action label representing the action of an entity depicted in a frame of a video.

U.S. Pat. App. Pub. No. 2017/0186226 discloses a calibration engine that uses a machine learning system to extracts a region of interest to compute values of shape parameters of a 3D mesh model.

U.S. Pat. App. Pub. No. 2017/0186226 discloses a system where an observed position is determined from an image and a predicted position is determined using an inertial measurement unit. The predicted position is adjusted by an offset until a difference between the observed position and the predicted position is less than a threshold value.

The disclosures of the above discussed patent documents are hereby incorporated herein by reference.

BRIEF DESCRIPTION OF THE DRAWINGS

The embodiments are illustrated by way of example and not limitation in the figures of the accompanying drawings in which like references indicate similar elements.

DETAILED DESCRIPTION

Figure 1:
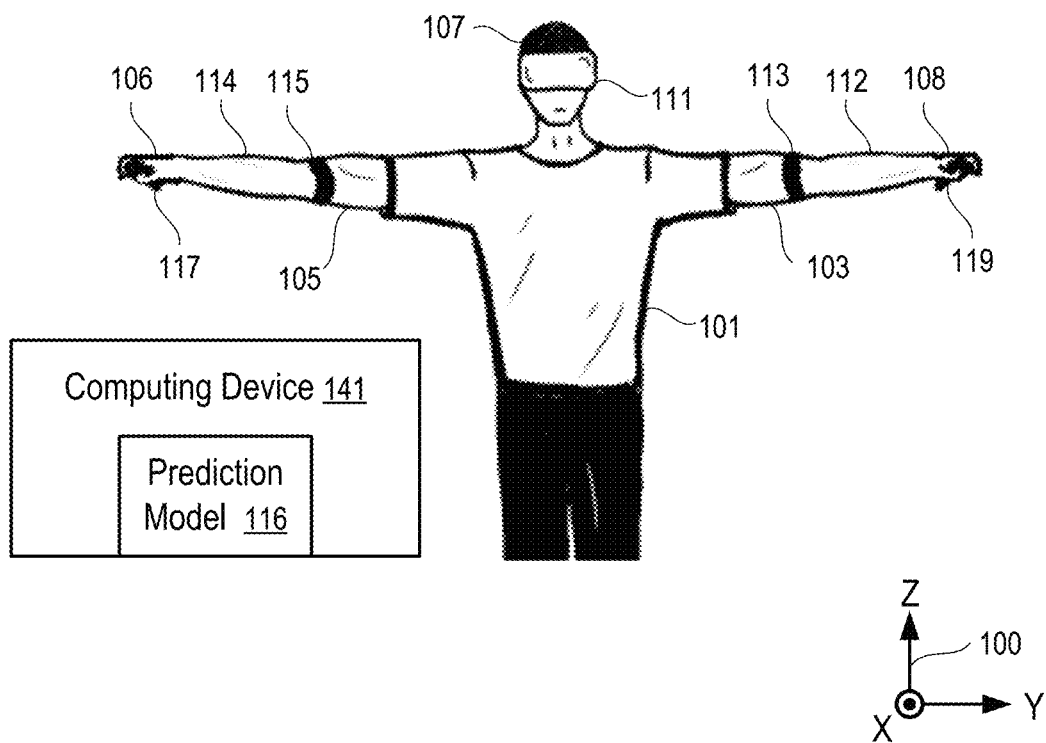
FIG. 1 illustrates a system to track user movements according to one embodiment.

The following description and drawings are illustrative and are not to be construed as limiting. Numerous specific details are described to provide a thorough understanding. However, in certain instances, well known or conventional details are not described to avoid obscuring the description. References to one or an embodiment in the present disclosure are not necessarily references to the same embodiment; and, such references mean at least one.

U.S. patent application Ser. No. 16/044,984, filed Jul. 25, 2018 and entitled "Calibration of Measurement Units in Alignment with a Skeleton Model to Control a Computer System," the entire disclosure of which is hereby incorporated herein by reference, discloses sensor modules having LED lights that can be used to provide optical indicators in the determination of the orientations of the sensor modules. A camera (e.g., in the head mounted display) can be used to capture images of the optical indicators to determine the orientations of the sensor modules. After identifying the locations of LED lights of sensor module in an image, the locations of the LED lights can be processed via an artificial neural network (ANN) to provide an orientation measurement for the sensor module. The orientation measurement for the sensor module, determined based on the optical indicators, can be used to calibrate orientation measurements generated by an inertial measurement unit in the sensor module.

In some instances, the LED lights of the sensor module may not be in a position visible to the camera and thus cannot be captured as optical indicators in the images generated by the camera. In other instances, the sensor module may not have LED lights configured on the sensor modules. The present application discloses techniques that can be used to determine orientation of the sensor module based on images captured in the camera, without relying upon LED optional indicators. For example, when the sensor module is being held or worn on a portion of the user in a predetermined manner, an image of the potion of the user can be used to in a first ANN to determine the orientation of predefined features of the user and then used in a second ANN to predict the orientation of the sensor module based on the orientations of the predefined features of the user. For example, the sensor module can be in a form of a ring worn on a predetermined finger of a hand of the user; and the first ANN can be used determine the orientations of features of the user, such as the orientations of the wrist, palm, forearm, and/or distal, middle and proximal phalanges of thumb and/or index finger of the user.

For example, a sensor device can be configured as a ring attached to the middle phalange of the index finger; and the sensor device has a touch pad. When the thumb of the user is placed on the touch pad of the sensor device, the orientation of the sensor device can be predicted based on the orientations of the bones of the thumb and/or the index finger. Thus, in response to the configuration of the thumb being on the touching pad of the sensor device worn on the middle phalange of the index finger, an image of the hand can be provided as an input to an ANN to determine the orientations of certain features on the hand of the user, which orientations can be used in a further ANN to determine the orientation of the ring/sensor device. For example, the features identified/used for the determination the orientation of the ring/sensor device can include bones and/or joints, such as wrist, palm, phalanges of thumb and index finger.

Once the orientation of sensor device is determined, calibration can be performed in a way similar to those disclosed in U.S. patent application Ser. No. 16/044,984, filed Jul. 25, 2018 and entitled "Calibration of Measurement Units in Alignment with a Skeleton Model to Control a Computer System," the entire disclosure of which is hereby incorporated herein by reference.

In general, uncalibrated measurements of an inertial measurement unit (IMU) can be considered as orientations of the inertial sensor measured relative to an unknown reference coordinate system. A calibration process identifies the unknown reference coordinate system and its relationship with respect to a known coordinate system. After the calibration the measurements of the IMU are relative to the known coordinate system. For example, the calibrated measurements can be an orientation relative to a predetermined orientation in the space, relative to a particular orientation of the sensor device at a specific time instance, relative to the orientation of the arm or hand of a user at a time instance, or relative to a reference orientation/pose of a skeleton model of the user.

In some embodiments, the determination of calibration parameters of the measurements of the inertial measurement unit such that the calibrated measurements of the inertial measurement unit are relative to a known orientation, such as the orientation of the sensor device in which the inertial measurement unit is installed, the orientation of the arm or hand of a user to which the sensor device is attached, or the orientation of a skeleton model of the user in a reference pose. For example, a stereo camera integrated in a head mount display (HMD) can be used to capture images of sensor modules on the user. In some embodiments, Computer vision techniques and/or artificial neural network techniques can process the captured images identify one or more orientations that can be used to calibrate the measurements of the inertial measurement units in the sensor modules.

In general, the kinematics of a user can be modeled using a skeleton model having a set of rigid parts/portions connected by joints. For example, the head, the torso, the left and right upper arms, the left and right forearms, the palms, phalange bones of fingers, metacarpal bones of thumbs, upper legs, lower legs, and feet can be considered as rigid parts that are connected via various joints, such as the neck, shoulders, elbows, wrist, and finger joints.

The movements of the parts in the skeleton model of a user can be controlled by the movements of the corresponding portions of the user tracked using sensor modules. The sensor modules can determine the orientations of the portions of the user, such as the hands, arms, and head of the user. The measured orientations of the corresponding parts of the user determine the orientations of the parts of the skeleton model, such as hands and arms. The relative positions and/or orientations of the rigid parts collectively represent the pose of the user and/or the skeleton model. The skeleton model of the user can be used to control the presentation of an avatar of the user, to identify the gesture inputs of the user, and/or to make a virtual realty or augmented reality presentation of the user.

FIG. 1 illustrates a system to track user movements according to one embodiment.

FIG. 1 illustrates various parts of a user, such as the torso (101) of the user, the head (107) of the user, the upper arms (103 and 105) of the user, the forearms (112 and 114) of the user, and the hands (106 and 108) of the user.

In an application illustrated in FIG. 1, the hands (106 and 108) of the user are considered rigid parts movable around the wrists of the user. In other applications, the palms and finger bones of the user can be further tracked for their movements relative to finger joints (e.g., to determine the hand gestures of the user made using relative positions among fingers of a hand and the palm of the hand).

In FIG. 1, the user wears several sensor modules/devices (111, 113, 115, 117 and 119) that track the orientations of parts of the user that are considered, or recognized as, rigid in an application.

In an application illustrated in FIG. 1, rigid parts of the user are movable relative to the torso (101) of the user and relative to each other. Examples of the rigid parts include the head (107), the upper arms (103 and 105), the forearms (112 and 114), and the hands (106 and 108). The joints, such as neck, shoulder, elbow, and/or wrist, connect the rigid parts of the user to form one or more kinematic chains. The kinematic chains can be modeled in a computing device (141) to control the application.

To track the relative positions/orientations of rigid parts in a kinematic chain that connects the rigid parts via one or more joints, a tracking device can be attached to each individual rigid part in the kinematic chain to measure its orientation.

In general, the position and/or orientation of a rigid part in a reference system (100) can be tracked using one of many systems known in the field. Some of the systems may use one or more cameras to take images of a rigid part marked using optical markers and analyze the images to compute the position and/or orientation of the part. Some of the systems may track the rigid part based on signals transmitted from, or received at, a tracking device attached to the rigid part, such as radio frequency signals, infrared signals, ultrasound signals. The signals may correspond to signals received in the tracking device, and/or signals emitted from the tracking device. Some of the systems may use inertial measurement units (IMUs) to track the position and/or orientation of the tracking device.

In FIG. 1, the sensor devices (111, 113, 115, 117 and 119) are used to track some of the rigid parts (e.g., 107, 103, 105, 106, 108) in the one or more kinematic chains, but sensor devices are omitted from other rigid parts (101, 112, 114) in the one or more kinematic chains to reduce the number of sensor devices used and/or to improve user experience for wearing the reduced number of sensor devices.

The computing device (141) can have a prediction model (141) trained to generate predicted measurements of parts (101, 112, 114, 107, 103, 105, 106, and/or 108) of the user based on the measurements of the sensor devices (111, 113, 115, 117 and 119).

For example, the prediction model (141) can be implemented using an artificial neural network (ANN) in the computing device (141) to predict the measurements of the orientations of the rigid parts (101, 112, 114) that have omitted sensor devices, based on the measurements of the orientations rigid parts (107, 103, 105, 106, 108) that have the attached sensor devices (111, 113, 115, 117 and 119).

Further, the artificial neural network can be trained to predict the measurements of the orientations of the rigid parts (107, 103, 105, 106, 108) that would be measured by another system (e.g., an optical tracking system), based on the measurement of the attached sensor devices (111, 113, 115, 117 and 119) that measure orientations using a different technique (e.g., IMUs).

The sensor devices (111, 113, 115, 117, 119) communicate their movement measurements to the computing device (141), which computes or predicts the orientation of the rigid parts (107, 103, 105, 106, 108, 101, 112, 114) by applying the measurements obtained from the attached sensor devices (111, 113, 115, 117 and 119) as inputs to an artificial neural network trained in a way as further discussed below.

In some implementations, each of the sensor devices (111, 113, 115, 117 and 119) communicates its measurements directly to the computing device (141) in a way independent from the operations of other sensor devices.

Alternative, one of the sensor devices (111, 113, 115, 117 and 119) may function as a base unit that receives measurements from one or more other sensor devices and transmit the bundled and/or combined measurements to the computing device (141). In some instances, the artificial neural network is implemented in the base unit and used to generate the predicted measurements that are communicated to the computing device (141).

Preferably, wireless connections made via a personal area wireless network (e.g., Bluetooth connections), or a local area wireless network (e.g., Wi-Fi connections) are used to facilitate the communication from the sensor devices (111, 113, 115, 117 and 119) to the computing device (141).

Alternatively, wired connections can be used to facilitate the communication among some of the sensor devices (111, 113, 115, 117 and 119) and/or with the computing device (141).

For example, a hand module (117 or 119) attached to or held in a corresponding hand (106 or 108) of the user may receive the motion measurements of a corresponding arm module (115 or 113) and transmit the motion measurements of the corresponding hand (106 or 108) and the corresponding upper arm (105 or 103) to the computing device (141).

The hand (106), the forearm (114), and the upper arm (105) can be considered a kinematic chain, for which an artificial neural network can be trained to predict the orientation measurements generated by an optical track system, based on the sensor inputs from the sensor devices (117 and 115) that are attached to the hand (106) and the upper arm (105), without a corresponding device on the forearm (114).

Optionally or in combination, the hand module (e.g., 117) may combine its measurements with the measurements of the corresponding arm module (115) to compute the orientation of the forearm connected between the hand (106) and the upper arm (105), in a way as disclosed in U.S. patent application Ser. No. 15/787,555, filed Oct. 18, 2017 and entitled "Tracking Arm Movements to Generate Inputs for Computer Systems", the entire disclosure of which is hereby incorporated herein by reference.

For example, the hand modules (117 and 119) and the arm modules (115 and 113) can be each respectively implemented via a base unit (or a game controller) and an arm/shoulder module discussed in U.S. patent application Pub. Ser. No. 15/492,915, filed Apr. 20, 2017 and entitled "Devices for Controlling Computers based on Motions and Positions of Hands", the entire disclosure of which application is hereby incorporated herein by reference.

In some implementations, the head module (111) is configured as a base unit that receives the motion measurements from the hand modules (117 and 119) and the arm modules (115 and 113) and bundles the measurement data for transmission to the computing device (141). In some instances, the computing device (141) is implemented as part of the head module (111). The head module (111) may further determine the orientation of the torso (101) from the orientation of the arm modules (115 and 113) and/or the orientation of the head module (111), using an artificial neural network trained for a corresponding kinematic chain, which includes the upper arms (103 and 105), the torso (101), and/or the head (107).

For the determination of the orientation of the torso (101), the hand modules (117 and 119) are optional in the system illustrated in FIG. 1.

Further, in some instances the head module (111) is not used in the tracking of the orientation of the torso (101) of the user.

Typically, the measurements of the sensor devices (111, 113, 115, 117 and 119) are calibrated for alignment with a common reference system, such as the coordinate system (100).

For example, the coordinate system (100) can correspond to the orientation of the arms and body of the user in a standardized pose illustrated in FIG. 1. When in the pose of FIG. 1, the arms of the user point in the directions that are parallel to the Y axis; the front facing direction of the user is parallel to the X axis; and the legs, the torso (101) to the head (107) are in the direction that is parallel to the Z axis.

After the calibration, the hands, arms (105, 103), the head (107) and the torso (101) of the user may move relative to each other and relative to the coordinate system (100). The measurements of the sensor devices (111, 113, 115, 117 and 119) provide orientations of the hands (106 and 108), the upper arms (105, 103), and the head (107) of the user relative to the coordinate system (100). The computing device (141) computes, estimates, or predicts the current orientation of the torso (101) and/or the forearms (112 and 114) from the current orientations of the upper arms (105, 103), the current orientation the head (107) of the user, and/or the current orientation of the hands (106 and 108) of the user and their orientation history using the prediction model (116).

Some techniques of using an artificial neural network to predict the movements of certain parts in a skeleton model that are not separately tracked using dedicated sensor devices can be found in U.S. patent application Ser. No. 15/996,389, filed Jun. 1, 2018 and entitled "Motion Predictions of Overlapping Kinematic Chains of a Skeleton Model used to Control a Computer System," and U.S. patent application Ser. No. 15/973,137, filed May 7, 2018 and entitled "tracking User Movements to Control a Skeleton Model in a Computer System," the entire disclosures of which applications are hereby incorporated herein by reference.

Optionally or in combination, the computing device (141) may further compute the orientations of the forearms from the orientations of the hands (106 and 108) and upper arms (105 and 103), e.g., using a technique disclosed in U.S. patent application Ser. No. 15/787,555, filed Oct. 18, 2017 and entitled "Tracking Arm Movements to Generate Inputs for Computer Systems", the entire disclosure of which is hereby incorporated herein by reference.

Figure 2:
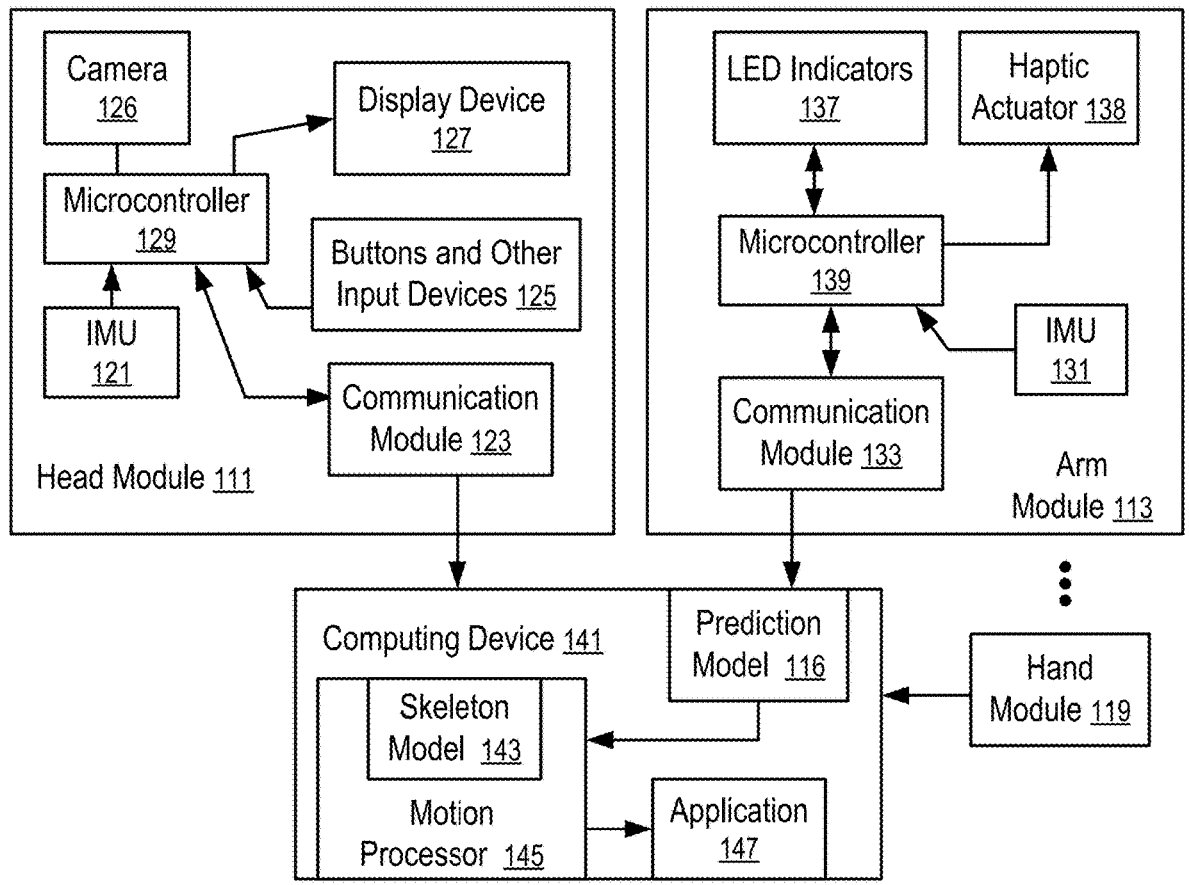
FIG. 2 illustrates a system to control computer operations according to one embodiment.

FIG. 2 illustrates a system to control computer operations according to one embodiment. For example, the system of FIG. 2 can be implemented via attaching the arm modules (115 and 113) to the upper arms (105 and 103) respectively, the head module (111) to the head (107) and/or hand modules (117 and 119), in a way illustrated in FIG. 1.

In FIG. 2, the head module (111) and the arm module (113) have micro-electromechanical system (MEMS) inertial measurement units (IMUs) (121 and 131) that measure motion parameters and determine orientations of the head (107) and the upper arm (103).

Similarly, the hand modules (117 and 119) can also have IMUs. In some applications, the hand modules (117 and 119) measure the orientation of the hands (106 and 108) and the movements of fingers are not separately tracked. In other applications, the hand modules (117 and 119) have separate IMUs for the measurement of the orientations of the palms of the hands (106 and 108), as well as the orientations of at least some phalange bones of at least some fingers on the hands (106 and 108). Examples of hand modules can be found in U.S. patent application Ser. No. 15/792,255, filed Oct. 24, 2017 and entitled "Tracking Finger Movements to Generate Inputs for Computer Systems," the entire disclosure of which is hereby incorporated herein by reference.

Each of the IMUs (131 and 121) has a collection of sensor components that enable the determination of the movement, position and/or orientation of the respective IMU along a number of axes. Examples of the components are: a MEMS accelerometer that measures the projection of acceleration (the difference between the true acceleration of an object and the gravitational acceleration); a MEMS gyroscope that measures angular velocities; and a magnetometer that measures the magnitude and direction of a magnetic field at a certain point in space. In some embodiments, the IMUs use a combination of sensors in three and two axes (e.g., without a magnetometer).

The computing device (141) can have a prediction model (116) and a motion processor (145). The measurements of the IMUs (e.g., 131, 121) from the head module (111), arm modules (e.g., 113 and 115), and/or hand modules (e.g., 117 and 119) are used in the prediction module (116) to generate predicted measurements of at least some of the parts that do not have attached sensor modules, such as the torso (101), and forearms (112 and 114). The predicted measurements and/or the measurements of the IMUs (e.g., 131, 121) are used in the motion processor (145).

Figure 3:
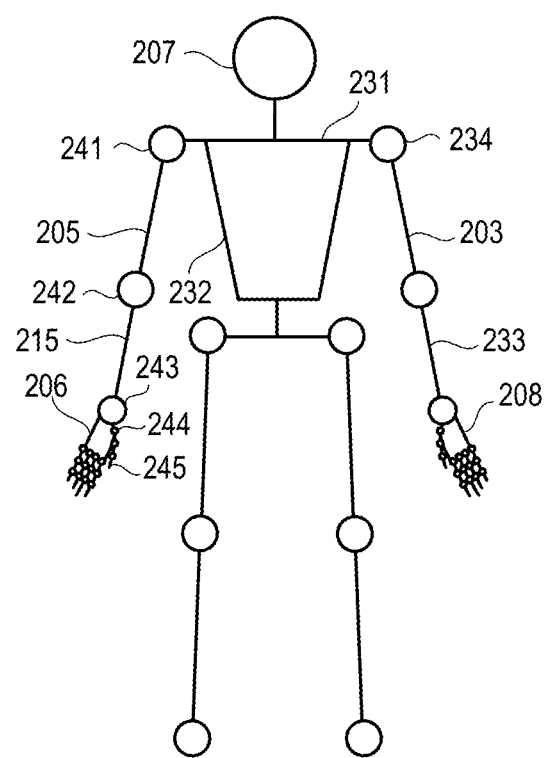
FIG. 3 illustrates a skeleton model that can be controlled by tracking user movements according to one embodiment.

The motion processor (145) has a skeleton model (143) of the user (e.g., illustrated FIG. 3). The motion processor (145) controls the movements of the parts of the skeleton model (143) according to the movements/orientations of the corresponding parts of the user. For example, the orientations of the hands (106 and 108), the forearms (112 and 114), the upper arms (103 and 105), the torso (101), the head (107), as measured by the IMUs of the hand modules (117 and 119), the arm modules (113 and 115), the head module (111) sensor modules and/or predicted by the prediction model (116) based on the IMU measurements are used to set the orientations of the corresponding parts of the skeleton model (143).

Since the torso (101) does not have a separately attached sensor module, the movements/orientation of the torso (101) can be predicted using the prediction model (116) using the sensor measurements from sensor modules on a kinematic chain that includes the torso (101). For example, the prediction model (116) can be trained with the motion pattern of a kinematic chain that includes the head (107), the torso (101), and the upper arms (103 and 105) and can be used to predict the orientation of the torso (101) based on the motion history of the head (107), the torso (101), and the upper arms (103 and 105) and the current orientations of the head (107), and the upper arms (103 and 105).

Similarly, since a forearm (112 or 114) does not have a separately attached sensor module, the movements/orientation of the forearm (112 or 114) can be predicted using the prediction model (116) using the sensor measurements from sensor modules on a kinematic chain that includes the forearm (112 or 114). For example, the prediction model (116) can be trained with the motion pattern of a kinematic chain that includes the hand (106), the forearm (114), and the upper arm (105) and can be used to predict the orientation of the forearm (114) based on the motion history of the hand (106), the forearm (114), the upper arm (105) and the current orientations of the hand (106), and the upper arm (105).

The skeleton model (143) is controlled by the motion processor (145) to generate inputs for an application (147) running in the computing device (141). For example, the skeleton model (143) can be used to control the movement of an avatar/model of the arms (112, 114, 105 and 103), the hands (106 and 108), the head (107), and the torso (101) of the user of the computing device (141) in a video game, a virtual reality, a mixed reality, or augmented reality, etc.

Preferably, the arm module (113) has a microcontroller (139) to process the sensor signals from the IMU (131) of the arm module (113) and a communication module (133) to transmit the motion/orientation parameters of the arm module (113) to the computing device (141). Similarly, the head module (111) has a microcontroller (129) to process the sensor signals from the IMU (121) of the head module (111) and a communication module (123) to transmit the motion/orientation parameters of the head module (111) to the computing device (141).

Optionally, the arm module (113) and the head module (111) have LED indicators (137 and 127) respectively to indicate the operating status of the modules (113 and 111).

Optionally, the arm module (113) has a haptic actuator (138) respectively to provide haptic feedback to the user.

Optionally, the head module (111) has a display device (127) and/or buttons and other input devices (125), such as a touch sensor, a microphone, a camera (126), etc.

In some instances, a stereo camera (126) is used to capture stereo images of the sensor devices (113, 115, 117, 119) to calibrate their measurements relative to a common coordinate system, such as the coordinate system (100) defined in connection with a reference pose illustrated in FIG. 1. Further, the LED indicators (e.g., 137) of a sensor module (e.g., 113) can be turned on during the time of capturing the stereo images such that the orientation and/or identity of the sensor module (e.g., 113) can be determined from the locations and/or patterns of the LED indicators.

When the LED lights are not captured in the images, or when the sensor device do not have LED lights, the orientation of the sensor module can be predicted based on an image of a portion of the user wearing the sensor device in a predefined manner. For example, an ANN can be used to determine the orientations of the wrist, palm, distal, middle and proximal phalanges of thumb and index finger from the image of the hand and forearm of the user; and the orientations can be further used in another ANN to determine the orientation of the sensor device.

In some implementations, the head module (111) is replaced with a module that is similar to the arm module (113) and that is attached to the head (107) via a strap or is secured to a head mount display device.

In some applications, the hand module (119) can be implemented with a module that is similar to the arm module (113) and attached to the hand via holding or via a strap. Optionally, the hand module (119) has buttons and other input devices, such as a touch sensor, a joystick, etc.

For example, the handheld modules disclosed in U.S. patent application Ser. No. 15/792,255, filed Oct. 24, 2017 and entitled "Tracking Finger Movements to Generate Inputs for Computer Systems", U.S. patent application Ser. No. 15/787,555, filed Oct. 18, 2017 and entitled "Tracking Arm Movements to Generate Inputs for Computer Systems", and/or U.S. patent application Ser. No. 15/492,915, filed Apr. 20, 2017 and entitled "Devices for Controlling Computers based on Motions and Positions of Hands" can be used to implement the hand modules (117 and 119), the entire disclosures of which applications are hereby incorporated herein by reference.

When a hand module (e.g., 117 or 119) tracks the orientations of the palm and a selected set of phalange bones, the motion pattern of a kinematic chain of the hand captured in the predictive mode (116) can be used in the prediction model (116) to predict the orientations of other phalange bones that do not wear sensor devices.

FIG. 2 shows a hand module (119) and an arm module (113) as examples. In general, an application for the tracking of the orientation of the torso (101) typically uses two arm modules (113 and 115) as illustrated in FIG. 1. The head module (111) can be used optionally to further improve the tracking of the orientation of the torso (101). Hand modules (117 and 119) can be further used to provide additional inputs and/or for the prediction/calculation of the orientations of the forearms (112 and 114) of the user.

Typically, an IMU (e.g., 131 or 121) in a module (e.g., 113 or 111) generates acceleration data from accelerometers, angular velocity data from gyrometers/gyroscopes, and/or orientation data from magnetometers. The microcontrollers (139 and 129) perform preprocessing tasks, such as filtering the sensor data (e.g., blocking sensors that are not used in a specific application), applying calibration data (e.g., to correct the average accumulated error computed by the computing device (141)), transforming motion/position/orientation data in three axes into a quaternion, and packaging the preprocessed results into data packets (e.g., using a data compression technique) for transmitting to the host computing device (141) with a reduced bandwidth requirement and/or communication time.

Each of the microcontrollers (129, 139) may include a memory storing instructions controlling the operations of the respective microcontroller (129 or 139) to perform primary processing of the sensor data from the IMU (121, 131) and control the operations of the communication module (123, 133), and/or other components, such as the LED indicators (137), the haptic actuator (138), buttons and other input devices (125), the display device (127), etc.

The computing device (141) may include one or more microprocessors and a memory storing instructions to implement the motion processor (145). The motion processor (145) may also be implemented via hardware, such as Application-Specific Integrated Circuit (ASIC) or Field-Programmable Gate Array (FPGA).

In some instances, one of the modules (111, 113, 115, 117, and/or 119) is configured as a primary input device; and the other module is configured as a secondary input device that is connected to the computing device (141) via the primary input device. A secondary input device may use the microprocessor of its connected primary input device to perform some of the preprocessing tasks. A module that communicates directly to the computing device (141) is consider a primary input device, even when the module does not have a secondary input device that is connected to the computing device via the primary input device.

In some instances, the computing device (141) specifies the types of input data requested, and the conditions and/or frequency of the input data; and the modules (111, 113, 115, 117, and/or 119) report the requested input data under the conditions and/or according to the frequency specified by the computing device (141). Different reporting frequencies can be specified for different types of input data (e.g., accelerometer measurements, gyroscope/gyrometer measurements, magnetometer measurements, position, orientation, velocity).

In general, the computing device (141) may be a data processing system, such as a mobile phone, a desktop computer, a laptop computer, a head mount virtual reality display, a personal medial player, a tablet computer, etc.

FIG. 3 illustrates a skeleton model that can be controlled by tracking user movements according to one embodiment. For example, the skeleton model of FIG. 3 can be used in the motion processor (145) of FIG. 2.

The skeleton model illustrated in FIG. 3 includes a torso (232) and left and right upper arms (203 and 205) that can move relative to the torso (232) via the shoulder joints (234 and 241). The skeleton model may further include the forearms (215 and 233), hands (206 and 208), neck, head (207), legs and feet. In some instances, a hand (206) includes a palm connected to phalange bones (e.g., 245) of fingers, and metacarpal bones of thumbs via joints (e.g., 244).

The positions/orientations of the rigid parts of the skeleton model illustrated in FIG. 3 are controlled by the measured orientations of the corresponding parts of the user illustrated in FIG. 1. For example, the orientation of the head (207) of the skeleton model is configured according to the orientation of the head (107) of the user as measured using the head module (111); the orientation of the upper arm (205) of the skeleton model is configured according to the orientation of the upper arm (105) of the user as measured using the arm module (115); and the orientation of the hand (206) of the skeleton model is configured according to the orientation of the hand (106) of the user as measured using the hand module (117); etc.

For example, the tracking system as illustrated in FIG. 2 measures the orientations of the modules (111, 113, . . . , 119) using IMUs (e.g., 111, 113, . . . ). The inertial-based sensors offer good user experiences, have less restrictions on the use of the sensors, and can be implemented in a computational efficient way. However, the inertial-based sensors may be less accurate than certain tracking methods in some situations, and can have drift errors and/or accumulated errors through time integration. Drift errors and/or accumulated errors can be considered as the change of the reference orientation used for the measurement from a known reference orientation to an unknown reference orientation. An update calibration can remove the drift errors and/or accumulated errors.

An optical tracking system can use one or more cameras (e.g., 126) to track the positions and/or orientations of optical markers (e.g., LED indicators (137)) that are in the fields of view of the cameras. When the optical markers are within the fields of view of the cameras, the images captured by the cameras can be used to compute the positions and/or orientations of optical markers and thus the orientations of parts that are marked using the optical markers. However, the optical tracking system may not be as user friendly as the inertial-based tracking system and can be more expensive to deploy. Further, when an optical marker is out of the fields of view of cameras, the positions and/or orientations of optical marker cannot be determined by the optical tracking system.

An artificial neural network of the prediction model (116) can be trained to predict the measurements produced by the optical tracking system based on the measurements produced by the inertial-based tracking system. Thus, the drift errors and/or accumulated errors in inertial-based measurements can be reduced and/or suppressed, which reduces the need for re-calibration of the inertial-based tracking system. Further details on the use of the prediction model (116) can be found in U.S. patent application Ser. No. 15/973,137, filed May 7, 2018 and entitled "tracking User Movements to Control a Skeleton Model in a Computer System," the entire disclosure of which application is hereby incorporated herein by reference.

Further, the orientations determined using images captured by the camera (126) can be used to calibrate the measurements of the sensor devices (111, 113, 115, 117, 119) relative to a common coordinate system, such as the coordinate system (100) defined using a standardized reference pose illustrated in FIG. 1, as further discussed below.

Figure 4:
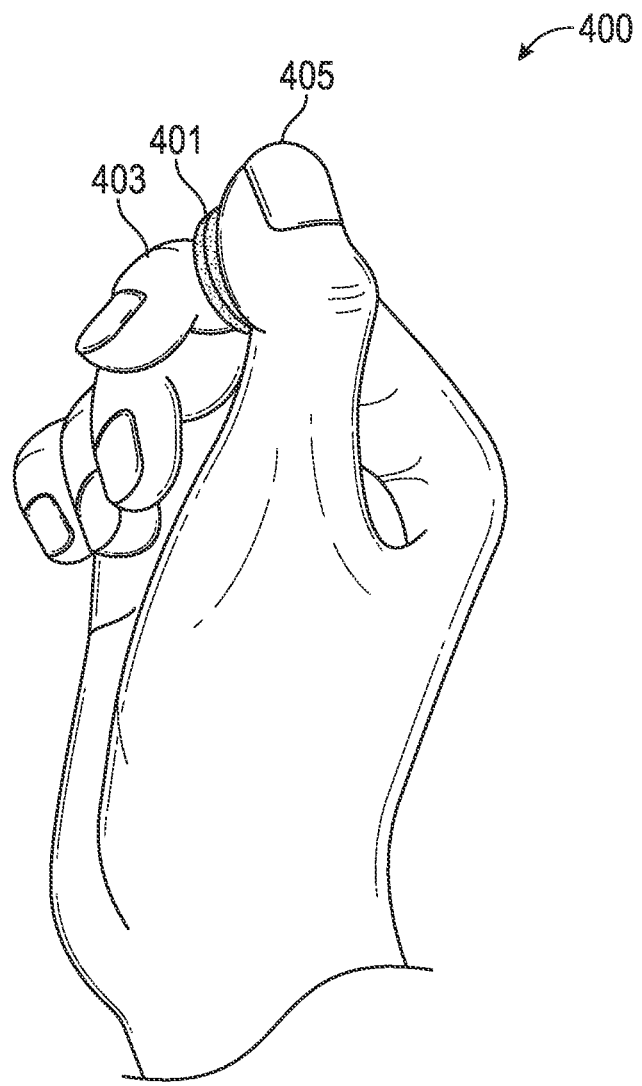
FIG. 4 illustrates a technique to determine an orientation of a ring device for tracking user movements using an image captured by a camera on a head mounted display according to some embodiments.

FIG. 4 illustrates a technique to determine an orientation of a ring device for tracking user movements using an image (400) captured by a camera (126) on a head mounted display (127) according to some embodiments. As illustrated in FIG. 4, a sensor device (401) is configured to have the form factor of a ring device suitable to be worn on a finger of a hand of the user. The sensor device (401) has an inertial measurement unit, similar to IMU (131) in an arm module (113). The sensor device (401) in the form of a ring can be worn on the middle phalange (403) of the index finger. The sensor device (401) is configured with a touch pad that can be ready touched by the thumb (405) to generate a touch input.

In some embodiments, the image (400) FIG. 4 captured by the camera (126) is converted into the image in a black/white format for processing to recognize the orientations of predefined features. For example, the image (400) FIG. 4 captured by the camera (126) can be processed by an ANN to determine the orientations of features, such as forearm, wrist, palm, distal phalange of thumb, middle phalange of thumb, distal phalange of index finger, middle phalange of index finger, proximal of index finger, and metacarpal of the index finger in palm connecting. Optionally, the system converts the original image (400) from higher resolution into a lower resolution image in a black/white format to facilitate the recognize.

The orientations of forearm, wrist, palm, distal phalanges, middle phalanges, and proximal phalange and determined from the image of the hand and upper arm illustrated in FIG. 4, can be provided as input to an ANN to predict the orientation of the sensor device (401). The predicted orientation can be used to calibrate the orientation measurement generated by the inertial measurement unit configured in the sensor device (401). Further, the relative orientations of the sensor device (401) and the hand of the user can be used to determine the orientation of the hand based on the orientation measurement generated by the inertial measurement unit configured in the sensor device (401).

Further details and examples of the technique of orientation determination based on FIG. 4 can be found in U.S. patent application Ser. No. 16/576,661, filed Sep. 19, 2019 and entitled "Calibration of Inertial Measurement Units in Alignment with a Skeleton Model to Control a Computer System based on Determination of Orientation of an Inertial Measurement Unit from an Image of a Portion of a User", the entire disclosure of which application is hereby incorporated herein by reference.

Figure 5:
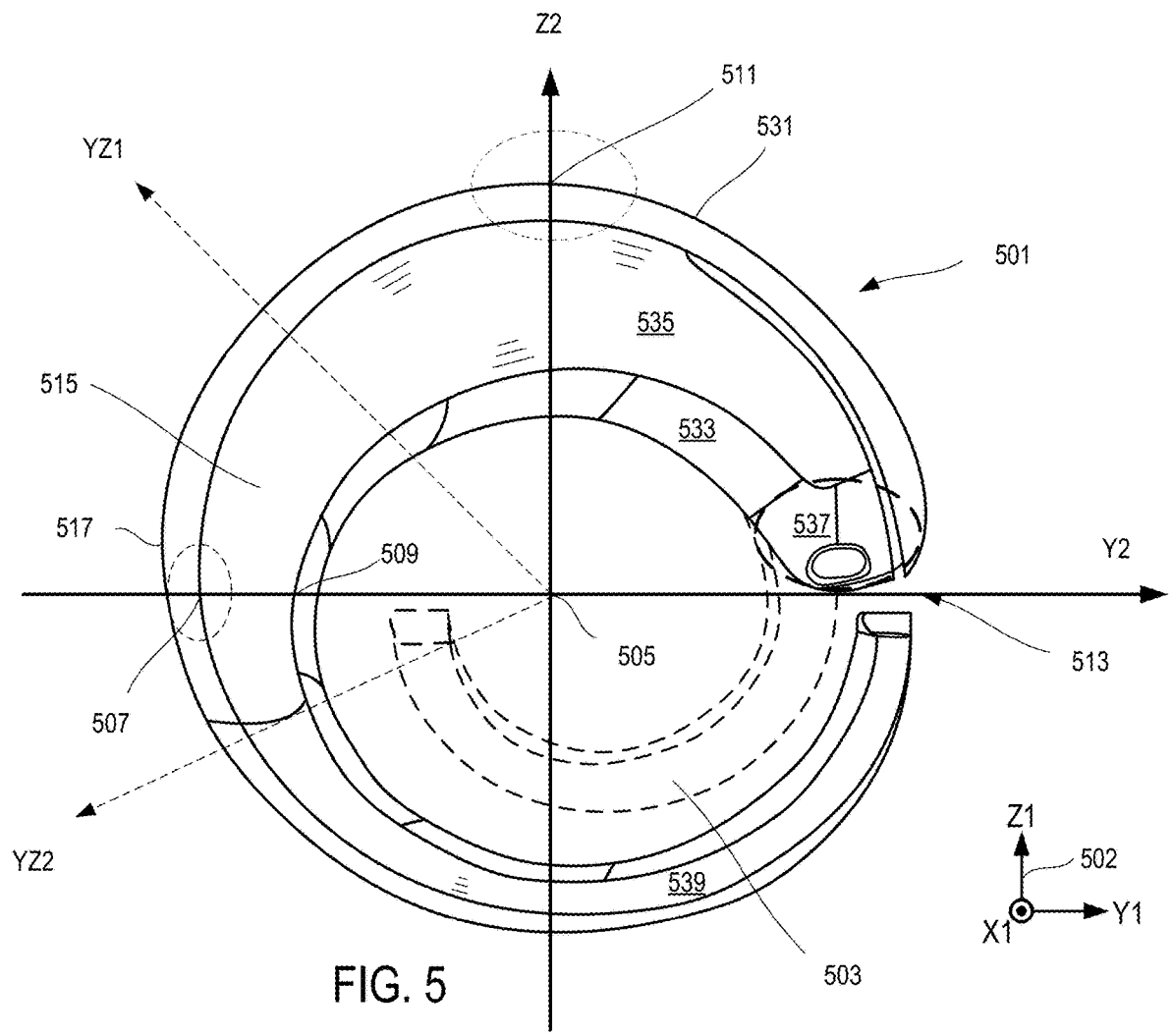
FIG. 5 shows a ring device having components configured at locations according to some embodiments.

FIG. 5 shows a ring device (501) having components configured at locations according to some embodiments. For example, the ring device (501) of FIG. 5 can have an inertial measurement unit, similar to the sensor device (401) of FIG. 4.

The ring device (501) of FIG. 5 has a ring-shaped housing configured to be wrapped round a finger of a user when the device (501) is worn on a finger of the user (e.g., in a way as illustrated in FIG. 4). The overall shape of the ring device (501) of FIG. 5 is substantially circular. In other embodiments, the overall shape of the ring device (501) can have other shapes (e.g., elliptical, octagonal, rectangular, triangular, etc.). The ring device (501) of FIG. 5 can be in one of many form-factors and can be configured include components similar to the hand module (119) or the arm module (113) illustrated in FIG. 2 as a part of the tracking system. In some implementations, the ring device (501) of FIG. 5 can be used to replace a hand module (119) in the system of FIG. 2, where the orientation measurements from the sensor modules (e.g., 501, 113, 111) are provided to a computing device (141) to control a skeleton model (143) of the user in a virtual reality application, a mixed reality application, an augmented reality application, etc. For example, the ring device (501) of FIG. 5 can provide orientation measurements to control the movement of parts of the skeleton model (143) of the user.

In FIG. 5, the ring device (501) can include a spring element (503) that extends from the housing of the ring device (501) for improved grip on the finger when the ring device (501) is worn on the finger.

Figure 6:
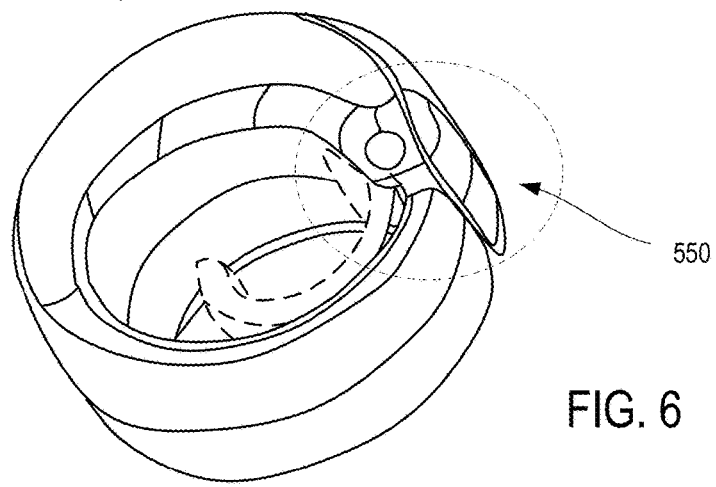
FIG. 6 shows another ring device according to some embodiments.

The ring device (501) of FIG. 5 having an overall "c" shape with an opening (513). The gap between the two ends of the "c" shape at the opening (513) can be small, or substantially closed in other implementations. FIG. 6 illustrates an alternative perspective view of the "c" shaped ring device of FIG. 5. In other embodiments, an optional joint can be configured near the two ends to substantially hide the gap between the two ends of the "c" shaped housing. For example, a joint (550) can be configured near the region (550) illustrated in FIG. 6. The housing of the ring device (501) of FIG. 5 (or FIG. 6) has structural discontinuity at the location near the opening (513).

At an opposite side (507) across the center (505) of the ring device (501) from the discontinuity point near the opening (513), the housing of the ring device (501) of FIG. 5 has a contiguous section (515).

In FIG. 5, the ring device (501) has a central axis X2 that is substantially in the direction of the lengthwise direction of a finger, when the ring device (501) is worn on the finger. The central axis X2 is at the center (505) of the ring device (501). The Y2 axis goes from the center (505) to the discontinuity point near the opening (513). The Z2 axis is perpendicular to the central axis X2 and the Y2 axis.

On the Y2 axis, the contiguous section (515) of the housing is at the opposite side of the center (505) relative to the discontinuity point at the opening (513).

In some embodiments, an antenna of the ring device (501) is configured (507) in the contiguous section (515) at a location (507) that is on or near the Y2 axis. The location (507) is substantially at in the middle of the contiguous section (515) that extends from line YZ1 to line YZ2 in FIG. 5. Lines YZ1 and Z2 form angles that are about 45 degrees from axis Z2. Lines YZ2 and Y2 form angles that are about 25 degrees from axis Y2. Lines YZ1 and YZ2 form angles that are about 70 degrees. The contiguous section (515) between the lines YZ1 and YZ2 can be considered a left section (515) when the discontinuity point at the opening (513) is considered to be located to the right of the center (505).

The contiguous section (515) has an outer portion (517) and an inner portion (509) that is closer to the finger or the center (505) than the outer portion (507). The antenna can be attached to the outer portion (517) of the contiguous section (515) near the location (507) to reduce skin effects and/or proximity effects.

The antenna of the ring device (501) can be configured to communicate with the computing device (141) using a Bluetooth Low Energy technique (BLE). For example, the antenna configured at the location (507) can be a ceramic antenna, a printed circuit board antenna, a stamped metal antenna, or a wire antenna. For example, the ring device (501) can be configured to transmit, via the BLE antenna to the computing device (141), data indicating of orientation of the finger based on measurements of the inertial measurement unit of the ring device (501). For example, the inertial measurement unit can include a micro-electromechanical system (MEMS) gyroscope, a MEMS accelerometer and/or a magnetometer.

In general, the location (507) of the BLE antenna is preferably closer to the outer portion of the housing and further away from the inner portion of the housing to reduce skin-effects and proximity effects. For example, when the BLE antenna is configured to be located at the contiguous section (515) between the lines YZ1 and YZ2, the BLE antenna is most protected from external effects and can function properly without being disrupted by other electronic components of the ring device (501), such as a touch pad, a charging pad, etc.

Some components of the ring device (501) can contain metal elements. The BLE antenna is isolated from such components that may disrupt the operations of the BLE antenna. For example, the contiguous section (515) can be made of a dielectric material to isolate the BLE antenna (507) from such components that are configured outside of the section (515) between the lines YZ1 and YZ2. In some embodiments, the metal contained materials should be away from the BLE antenna at the distance which is no less than 3 mm. Therefore, the dielectric material can be smaller than the section (515) based on the location of the BLE antenna. The dielectric material can include one or more types of plastic such as Acrylonitrile Butadiene Styrene (ABS), Polypropylene (PP), Polycarbonates (PC), Polymethyl Methacrylate (PMMA), Polyethylene (PE), Polystyrene (PS), High Impact Polystyrene (HIPS), Thermoplastic Elastomer (TPE), Thermoplastic polyurethane (TPU), or Silicone, or any combination thereof.

Optionally, the ring device (501) has a light-emitting diode (LED) indicator configured at a location (511) that is on or near the Z2 axis and in an outer portion (531) of an upper contiguous section of the housing of the ring device (501). In some embodiments, the ring device (501) can have a light-emitting diode (LED) indicator configured at any portion (531, 533, 535)) of an upper contiguous section of the housing of the ring device (501).

In FIG. 5, the upper contiguous section (531, 533, 535) is above the center (505) and is between the positive portion of axis Y2 and the line YZ1. The angle between the positive portion of axis Y2 and the line YZ1 is about 135 degrees in a cross-section view of the housing. For example, the upper contiguous section can include an outer portion (531), a middle portion (535), and an inner portion (533) that is closer to the center (505) than the middle portion (535) and the outer portion (531).

Optionally, the ring device (501) has a charging pad (533, 537, 539) configured to charge a battery configured in the ring device (501). For example, the charging pad (533, 537) can be configured in the upper part of the device at the inner portion (533, 537) of the upper contiguous section. Alternatively, the charging pad (537) can be configured in the lower contiguous section (539) that is between the positive portion of axis Y2 and the line YZ2. An angle between the positive portion of axis Y2 and the line YZ2 is no more than 155 degrees.

Optionally, the ring device (501) has a touch pad configured to receive touch input from a finger of the user. For example, the touch pad can be configured on the outer portion (531) of the upper contiguous section between the positive portion of axis Y2 and the positive portion of axis Z2. Thus, the touch pad extends no more than 90 degrees from the positive portion of axis Y2.

Optionally, the ring device (501) has an LED display configured to present output data to the user. For example, the LED display can be configured on the outer portion (531) of the upper contiguous section between the positive portion of axis Y2 and the positive portion of axis Z2. Thus, the LED display extends no more than 90 degrees from the positive portion of axis Y2.

Optionally, the ring device (501) has a fingerprint scanner configured to generate fingerprint data of the user of the ring device (501) to identify the user. For example, the fingerprint scanner can be configured on the outer portion (531) of the upper contiguous section between the positive portion of axis Y2 and the positive portion of axis Z2. Thus, the fingerprint scanner extends no more than 90 degrees from the positive portion of axis Y2

Optionally, the ring device (501) has a force sensor configured to detect the pressure of touch or click of the user while interacting with device. For example, the force sensor can be configured on the outer portion (531) of the upper contiguous section between the positive portion of axis Y2 and the positive portion of axis Z2. Thus, the force sensor extends no more than 90 degrees from the positive portion of axis Y2.

Optionally, the ring device (501) has a near field communication (NFC) marker configured to provide identification information through NFC communications. In some embodiments, the NFC maker can be configured in the lower contiguous section (539) that is between the positive portion of axis Y2 and the line YZ2. An angle between the positive portion of axis Y2 and the line YZ2 is no more than 135 degrees Optionally, the ring device (501) has one or more biosensor components configured on an inner portion (533) of the upper contiguous section between the positive portion of axis Y2 and the line YZ1. An angle between the positive portion of axis Y2 and the line YZ1 is no more than 155 degrees.

For example, the one or more biosensor components can include heart rate sensor (i.e., optical heart rate sensor/photoplethysmography sensor) to measure heart rate in beats per minute or detect the pulse waves; piezoelectrical sensors to measure changes in pressure, acceleration, temperature, strain, or force; capacitive and/or optical sensors to detect if the user was wearing the device (500) and to detect and measure proximity of nearby objects; thermometer to measure temperature of the user; Manometer to measure blood pressure; galvanic skin sensor to measure skin resistance, skin conductance and stress level (i.e., sweating); electromyography sensor to measure the electrical activity of muscles; and/or CGM (continuous glucose monitoring) sensor to monitor glucose level.

Optionally, the ring device (501) has a microphone configured to collect voice inputs from a user for transmission to the computing device (141). In some embodiments, the microphone can be configured on the middle portion (535) of the upper contiguous section between the positive portion of axis Y2 and the line YZ1. An angle between the positive portion of axis Y2 and the line YZ1 is no more than 135 degrees.

Optionally, the ring device (501) has a haptic actuator and/or speaker configured present the output feedback to its user. In some embodiments, the haptic actuator and/or speaker can be configured on the middle portion (535) of the upper contiguous section between the positive portion of axis Y2 and the line YZ1. An angle between the positive portion of axis Y2 and the line YZ1 is no more than 135 degrees.

The present disclosure includes methods and apparatuses which perform these methods, including data processing systems which perform these methods, and computer readable media containing instructions which when executed on data processing systems cause the systems to perform these methods.

For example, the computing device (141), the arm modules (113, 115) and/or the head module (111) can be implemented using one or more data processing systems.

A typical data processing system may include an inter-connect (e.g., bus and system core logic), which interconnects a microprocessor(s) and memory. The microprocessor is typically coupled to cache memory.

The inter-connect interconnects the microprocessor(s) and the memory together and also interconnects them to input/output (I/O) device(s) via I/O controller(s). I/O devices may include a display device and/or peripheral devices, such as mice, keyboards, modems, network interfaces, printers, scanners, video cameras and other devices known in the art. In one embodiment, when the data processing system is a server system, some of the I/O devices, such as printers, scanners, mice, and/or keyboards, are optional.

The inter-connect can include one or more buses connected to one another through various bridges, controllers and/or adapters. In one embodiment the I/O controllers include a USB (Universal Serial Bus) adapter for controlling USB peripherals, and/or an IEEE-1394 bus adapter for controlling IEEE-1394 peripherals.

The memory may include one or more of: ROM (Read Only Memory), volatile RAM (Random Access Memory), and non-volatile memory, such as hard drive, flash memory, etc.

Volatile RAM is typically implemented as dynamic RAM (DRAM) which requires power continually in order to refresh or maintain the data in the memory. Non-volatile memory is typically a magnetic hard drive, a magnetic optical drive, an optical drive (e.g., a DVD RAM), or other type of memory system which maintains data even after power is removed from the system. The non-volatile memory may also be a random access memory.

The non-volatile memory can be a local device coupled directly to the rest of the components in the data processing system. A non-volatile memory that is remote from the system, such as a network storage device coupled to the data processing system through a network interface such as a modem or Ethernet interface, can also be used.

In the present disclosure, some functions and operations are described as being performed by or caused by software code to simplify description. However, such expressions are also used to specify that the functions result from execution of the code/instructions by a processor, such as a microprocessor.

Alternatively, or in combination, the functions and operations as described here can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

While one embodiment can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Routines executed to implement the embodiments may be implemented as part of an operating system or a specific application, component, program, object, module or sequence of instructions referred to as "computer programs." The computer programs typically include one or more instructions set at various times in various memory and storage devices in a computer, and that, when read and executed by one or more processors in a computer, cause the computer to perform operations necessary to execute elements involving the various aspects.

A machine readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine readable medium in entirety at a particular instance of time.

Examples of computer-readable media include but are not limited to non-transitory, recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROM), Digital Versatile Disks (DVDs), etc.), among others. The computer-readable media may store the instructions.

The instructions may also be embodied in digital and analog communication links for electrical, optical, acoustical or other forms of propagated signals, such as carrier waves, infrared signals, digital signals, etc. However, propagated signals, such as carrier waves, infrared signals, digital signals, etc. are not tangible machine readable medium and are not configured to store instructions.

In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. An apparatus, comprising:
a c-shaped housing configured to be wrapped round a finger of a user, the c-shaped housing having an opening or a joint at a first point round the finger and a first contiguous section that is at a location opposite to the first point across a central axis of the c-shaped housing, wherein at least the first contiguous section is made of a dielectric material;
an antenna configured in an outer portion of the c-shaped housing in the first contiguous section, the outer portion further from a center of the c-shaped housing than an inner portion; and
a spring element that extends from one end of the c-shaped housing configured to grip the finger of the user when the c-shaped housing is wrapped round the finger of the user.

2. The apparatus of claim 1, wherein the antenna is configured to communicate using a Bluetooth Low Energy technique,
wherein the first contiguous section has an outer portion and an inner portion that is closer to the finger than the outer portion; and the antenna is attached to an outer portion of the first contiguous section, and
wherein a line passing through a location of the antenna and the first point goes through the central axis of the c-shaped housing and a center of a cross-section of the finger.

3. The apparatus of claim 2, further comprising:
an inertial measurement unit configured to measure motions of the finger;
wherein the apparatus is configured to transmit, via the antenna to a computing device, data indicating of orientation of the finger based on measurements of the inertial measurement unit.

4. The apparatus of claim 3, wherein the inertial measurement unit includes a micro-electromechanical system (MEMS) gyroscope, a MEMS accelerometer and a magnetometer.

5. The apparatus of claim 4, further comprising:
a light-emitting diode (LED) indicator configured on an outer portion of the c-shaped housing.

6. The apparatus of claim 5, wherein a line passing through the light-emitting diode (LED) indicator and the central axis of the c-shaped housing is substantially orthogonal to the line passing through the location of the antenna and the first point.

7. The apparatus of claim 4, further comprising:
a charging pad configured to charge a battery configured in the c-shaped housing, the charging pad being configured at the first point.

8. The apparatus of claim 4, further comprising:
a charging pad configured to charge a battery configured in the c-shaped housing, the charging pad being configured on the c-shaped housing between the first point and the antenna and at a location that is no more than 135 degrees from the first point in a cross-section of the c-shaped housing in a plane that is perpendicular to the central axis;
wherein the central axis is in a lengthwise direction of the finger.

9. The apparatus of claim 4, further comprising:
a touch pad configured to receive touch input from the finger of the user, the touch pad being configured on the c-shaped housing between the first point and the antenna and at a location that is no more than 90 degrees from the first point in a cross-section of the c-shaped housing in a plane that is perpendicular to the central axis.

10. The apparatus of claim 4, further comprising:
one or more first devices configured on an outer portion of the c-shaped housing, the one or more first devices including a light-emitting diode (LED) display, a finger print scanner, a force sensor, or any combination thereof.

11. The apparatus of claim 4, further comprising:
a Near Field Communication (NFC) marker configured to charge a battery configured in the c-shaped housing, the NFC marker being configured on the c-shaped housing between the first point and the antenna and at a location that is no more than 135 degrees from the first point in a cross-section of the c-shaped housing in a plane that is perpendicular to the central axis;
wherein the central axis is in a lengthwise direction of the finger.

12. The apparatus of claim 4, further comprising:
one or more second devices configured on a middle portion of the c-shaped housing, wherein the one or more second devices including a Haptic actuator, a speaker, a microphone or any combination thereof.

13. The apparatus of claim 4, wherein the dielectric material includes one or more types of plastic, the dielectric material including Acrylonitrile Butadiene Styrene (ABS), Polypropylene (PP), Polycarbonates (PC), Polymethyl Methacrylate (PMMA), Polyethylene (PE), Polystyrene (PS), High Impact Polystyrene (HIPS), Thermoplastic Elastomer (TPE), Thermoplastic polyurethane (TPU), or Silicone, or any combination thereof.

14. The apparatus of claim 6, wherein the antenna is a ceramic antenna, a printed circuit board antenna, a stamped metal antenna, or a wire antenna.

15. An apparatus, comprising:
a housing having a c-shape and configured to be wrapped round a finger of a user, the housing having a central axis in a lengthwise direction of the finger, the housing having an opening or joint along a circumferential direction, the housing having:
an upper portion above a first plane passing through the central axis and the opening or joint, and
a lower portion below the first plane;
a Bluetooth antenna configured in a contiguous portion of the housing that connects the upper portion and the lower portion, wherein the Bluetooth antenna is disposed in an outer portion of the housing that is further from a center of the housing than an inner portion; and
a spring element that extends from one end of the housing and configured to grip the finger of the user when the housing is wrapped round the finger of the user.

16. The apparatus of claim 15, further comprising:
an inertial measurement unit configured to measure motions of the finger;
wherein the apparatus is configured to transmit, via the Bluetooth antenna to a computing device, data indicating of orientation of the finger based on measurements of the inertial measurement unit.

17. The apparatus of claim 16, wherein a second plane passing through the central axis and perpendicular to the first plane divides the housing into a left portion and a right portion; wherein the Bluetooth antenna is located in the left portion, and the opening or joint is located in the right portion; and wherein the apparatus further comprises:
a touch pad configured on the right portion and on the upper portion; and
a charging pad configured on an end of the opening, or lower portion.

18. An apparatus, comprising:
a housing having a c-shape and configured to be wrapped round a finger of a user, the housing having a central axis in a lengthwise direction of the finger, the housing having an opening or joint along a circumferential direction, the housing having:
a first section spanning from the opening or joint up to 90 degrees in the circumferential direction;
a second section spanning from the opening or joint up to 135 degrees in the circumferential direction opposite to the first section; and
a third section connecting between the first section and the second section contiguously;
an inertial measurement unit having a micro-electromechanical system (MEMS) gyroscope;
a Bluetooth antenna configured in an outer portion of the third section at a location that is farthest from the opening or joint, the Bluetooth antenna configured to transmit orientation data of the apparatus as measured using the MEMS gyroscope;
a spring element that extends from one end of the housing and configured to grip the finger of the user when the housing is wrapped round the finger of the user; and
a touch pad configured on an outer portion of the first section.

19. The apparatus of claim 18, further comprising:
a charging pad configured on the second section or on the first section at an end near the opening.

20. The apparatus of claim 19, further comprising:
a light-emitting diode (LED) indicator configured at an outer portion of the housing where the first section meets the third section.

* * * * *